(12) United States Patent
De Boer et al.

(10) Patent No.: US 8,252,874 B2
(45) Date of Patent: Aug. 28, 2012

(54) LIGANDS AND CATALYST SYSTEMS FOR THE OLIGOMERIZATION OF OLEFINIC MONOMERS

(75) Inventors: Eric Johannes Maria De Boer, Amsterdam (NL); Harry Van Der Heijden, Amsterdam (NL); Quoc An On, Amsterdam (NL); Johan Paul Smit, Amsterdam (NL); Arie Van Zon, Amsterdam (NL)

(73) Assignee: Shell Oil Company, Houston, TX (US)

( * ) Notice: Subject to any disclaimer, the term of this patent is extended or adjusted under 35 U.S.C. 154(b) by 820 days.

(21) Appl. No.: 11/961,719

(22) Filed: Dec. 20, 2007

(65) Prior Publication Data

US 2009/0069517 A1 Mar. 12, 2009

(30) Foreign Application Priority Data

Dec. 22, 2006 (EP) .................................. 06256570

(51) Int. Cl.
*C08F 4/06* (2006.01)

(52) U.S. Cl. ........ 526/145; 502/167; 544/157; 560/138; 564/12

(58) Field of Classification Search .................... None
See application file for complete search history.

(56) References Cited

U.S. PATENT DOCUMENTS

| | | | | |
|---|---|---|---|---|
| 5,198,563 | A | 3/1993 | Reagen et al. | 556/57 |
| 5,523,507 | A | 6/1996 | Reagen et al. | 585/513 |
| 5,811,618 | A | 9/1998 | Wu | 585/513 |
| 5,968,866 | A | 10/1999 | Wu | 502/155 |
| 6,800,702 | B2 | 10/2004 | Wass | 526/124.3 |
| 7,141,633 | B2 | 11/2006 | Wass | 526/124.3 |
| 7,217,842 | B2 * | 5/2007 | Schanen et al. | 568/10 |
| 7,273,959 | B2 | 9/2007 | Drent et al. | 585/514 |
| 7,297,832 | B2 | 11/2007 | Blann et al. | 585/527 |
| 2003/0166456 | A1 | 9/2003 | Wass | 502/102 |
| 2005/0113622 | A1 | 5/2005 | Drent et al. | 585/521 |
| 2006/0128910 | A1 | 6/2006 | Blann et al. | 526/160 |
| 2006/0173226 | A1 | 8/2006 | Blann et al. | 585/511 |
| 2006/0211903 | A1 | 9/2006 | Blann et al. | 585/511 |
| 2006/0229480 | A1 | 10/2006 | Blann et al. | 585/535 |
| 2009/0062493 | A1 | 3/2009 | De Boer et al. | 526/145 |
| 2010/0311928 | A1 | 12/2010 | De Boer et al. | 526/145 |
| 2010/0311929 | A1 | 12/2010 | De Boer et al. | 526/145 |
| 2010/0311932 | A1 | 12/2010 | De Boer et al. | 526/172 |
| 2010/0317814 | A1 | 12/2010 | De Boer et al. | 526/145 |

FOREIGN PATENT DOCUMENTS

| | | |
|---|---|---|
| CN | 1651142 | 8/2005 |
| JP | 2003088760 | 3/2003 |
| WO | WO2002004119 | 1/2002 |
| WO | WO2004056478 | 7/2004 |
| WO | WO2004056479 | 7/2004 |
| WO | WO2005039758 | 5/2005 |
| WO | WO2005123884 | 12/2005 |

OTHER PUBLICATIONS

Fei et al., {Understanding Structure Does Not Always Explain Reactivity: A Phosphinoamide Anion Reacts as an Iminophosphide Anion, Inorganic Chemistry (2003), 42(6), 2125-2130}.*
Carter A et al: "High activity ethylene trimerisation catalysts based on diphosphine ligands". Chemical Communications—CHEMCOM, Royal Society of Chemstry, GB, vol. 2002, No. 8, Mar. 20, 2002, pp. 858-859, XP002277009. ISSN: 1359-7345.
M J Overett et al., "Ethylene trimerisation and tetramerisation catalysts with polar-substituted diphosphinoamine ligands," Chem. Commun., vol. 5, 2005, pp. 622-624.
V L Foss et al., "Tetraalkyldiphosphine Imides and the Isomeric Diphosphazanes," J. Gen. Chem. USSR, vol. 54, No. 12, 1984, pp. 2386-2399.
L E Anagho et al., "Synthesis and Solid-State Structure of a Metal Complex of a Diphosphineimine," Angewandte Chemie, Int. Ed., vol. 44, 2005, pp. 3271-3275.

* cited by examiner

*Primary Examiner* — Elvis O Price

(57) ABSTRACT

The present invention relates to ligands and catalyst systems and a process for the simultaneous trimerization and tetramerization of olefinic monomers using said ligands, the ligands having the general formula (I):

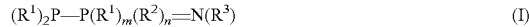

$(R^1)_2P—P(R^1)_m(R^2)_n=N(R^3)$ (I)

wherein $R^3$ is selected from hydrogen, a hydrocarbyl group, a substituted hydrocarbyl group, a heterohydrocarbyl group, a substituted heterohydrocarbyl group, a silyl group or derivative thereof;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2.

19 Claims, No Drawings

LIGANDS AND CATALYST SYSTEMS FOR THE OLIGOMERIZATION OF OLEFINIC MONOMERS

FIELD OF THE INVENTION

The present invention relates to ligands and to catalyst systems comprising said ligands. The present invention further relates to a process for the oligomerization of olefinic monomers using said catalyst systems.

BACKGROUND OF THE INVENTION

The efficient catalytic trimerization or tetramerization of olefinic monomers, such as the trimerization and tetramerization of ethylene to 1-hexene and 1-octene, is an area of great interest for the production of olefinic trimers and tetramers of varying degrees of commercial value. In particular, 1-hexene is a valuable comonomer for linear low-density polyethylene (LLDPE) and 1-octene is valuable as a chemical intermediate in the production of plasticizer alcohols, fatty acids, detergent alcohol and lubrication oil additives as well as a valuable comonomer in the production of polymers such as polyethylene. 1-Hexene and 1-octene can be produced by a conventional transition metal oligomerization process, although the trimerization and tetramerization routes are preferred.

Several different catalytic systems have been disclosed in the art for the trimerization of ethylene to 1-hexene. A number of these catalysts are based on chromium.

U.S. Pat. No. 5,198,563 (Phillips) discloses chromium-based catalysts containing monodentate amine ligands useful for trimerizing olefins.

U.S. Pat. No. 5,968,866 (Phillips) discloses an ethylene oligomerization/trimerization process which uses a catalyst comprising a chromium complex which contains a coordinating asymmetric tridentate phosphane, arsane or stibane ligand and an aluminoxane to produce alpha-olefins which are enriched in 1-hexene.

U.S. Pat. No. 5,523,507 (Phillips) discloses a catalyst based on a chromium source, a 2,5-dimethylpyrrole ligand and an alkyl aluminium activator for use in the trimerization of ethylene to 1-hexene.

Chem. Commun., 2002, 8, 858-859 (BP), discloses chromium complexes of ligands of the type $Ar_2PN(Me)PAr_2$ (Ar=ortho-methoxy-substituted aryl group) as catalysts for the trimerization of ethylene.

U.S. Pat. No. 7,141,633 (BP) discloses a catalyst for the trimerization of olefins comprising a source of chromium, molybdenum or tungsten, a ligand containing at least one phosphorus, arsenic or antimony atom bound to at least one hydrocarbyl or heterohydrocarbyl group having a polar substituent, but excluding the case where all such polar substituents are phosphane, arsane or stibane groups, and optionally an activator. The ligand used in most of the examples is $(2\text{-methoxyphenyl})_2PN(Me)P(2\text{-methoxyphenyl})_2$.

Although the catalysts disclosed in the BP documents mentioned above have good selectivity for 1-hexene within the $C_6$ fraction, a relatively high level of by-product formation (e.g. $C_{10}$ by-products) is typically observed.

U.S. Pat. No. 7,273,959 (Shell) discloses a trimerization catalyst composition and a process for the trimerization of olefinic monomers using said catalyst composition.

Catalytic systems for the tetramerization of ethylene to 1-octene have recently been described. A number of these catalysts are based on chromium.

U.S. Published Patent Applications Nos. 2006/0128910, 2006/0173226, 2006/0211903, and 2006/0229480 (Sasol) disclose catalyst compositions and processes for the tetramerization of olefins. The catalyst compositions disclosed comprise a transition metal and a heteroatomic ligand having the general formula $(R)_nA\text{-}B\text{---}C(R)_m$ where A and C are independently selected from a group which comprises phosphorus, arsenic, antimony, oxygen, bismuth, sulphur, selenium, and nitrogen, and B is a linking group between A and C, and R is independently selected from any homo or heterohydrocarbyl group of which at least one R group is substituted with a polar substituent and n and m are determined by the respective valence and oxidation state of A and/or C. The other catalyst compositions disclosed comprise a transition metal and a heteroatomic ligand having the general formula $(R')_nA\text{-}B\text{---}C(R')_m$ where A, B, C, n and m are as defined above, and R' is independently selected from any homo or heterohydrocarbyl group.

Example 16 of U.S. Published Patent Application No. 2006/0173226 discloses an ethylene tetramerization reaction using Cr(III)acetylacetonate, $(\text{phenyl})_2PN(\text{isopropyl})P(2\text{-methoxyphenyl})_2$ in a ratio of 1:2 mol/mol, and MAO, with an Al:Cr atomic ratio of 136:1, at 45° C. and 45 barg. However, the reaction produced a product composition with over 24 wt % of the products having greater than 11 carbon atoms, based on the weight of all products (9.00 wt % $C_{11}$+liquids and 15.11 wt % solids).

U.S. Published Patent Application No. 2006/0128910 (Sasol) discloses the tandem tetramerization and polymerisation of ethylene. Specifically, it discloses a process for polymerising olefins to produce branched polyolefins in the presence of a distinct polymerization catalyst and a distinct tetramerization catalyst, wherein the tetramerization catalyst produces 1-octene in a selectivity greater than 30% and the 1-octene produced is at least partially incorporated into the polyolefin chain.

Although the tetramerization catalysts disclosed in the Sasol documents mentioned above have good selectivity for 1-octene within the $C_8$ fraction, again, a relatively high level of by-product formation is observed. Typically, the by-product consists of $C_6$ compositions; however, only about 70 to 80% wt. of the $C_6$ by-product composition is 1-hexene, with the remaining $C_6$ by-product comprising compounds such as methylcyclopentane and methylenecyclopentane. The presence of these remaining $C_6$ by-product compositions, which have very little commercial use or value, is highly undesirable from both an economic point of view as well as from a product separation point of view.

It has now been surprisingly found that the ligands and catalyst systems of the present invention provide excellent results in the trimerization and tetramerization of olefinic monomers. In particular the selective production of 1-hexene and 1-octene from ethylene is achieved while reducing the level of by-product formation, especially $C_{10}$ by-products, solids (i.e. heavy waxes and/or polyethylene) and $C_6$ compositions/isomers other than 1-hexene.

SUMMARY OF THE INVENTION

According to the present invention there is provided a ligand having the general formula (I):

$$(R^1)_2P\text{---}P(R^1)_m(R^2)_n\text{===}N(R^3) \quad\quad (I)$$

wherein $R^3$ is selected from hydrogen, a hydrocarbyl group, a substituted hydrocarbyl group, a heterohydrocarbyl group, a substituted heterohydrocarbyl group, a silyl group or derivative thereof;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2.

According to another aspect of the present invention there is provided a ligand having the general formula (II):

$$P(R^1)_m(R^2)_n—P(R^1)_2=N(R^3) \quad (II)$$

wherein $R^3$ is selected from hydrogen, a hydrocarbyl group, a substituted hydrocarbyl group, a heterohydrocarbyl group, a substituted heterohydrocarbyl group, a silyl group or derivative thereof;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2.

According to a further aspect of the present invention there is a provided a process for preparing a ligand having the general formulae (I) or (II) which comprises reacting:
(i) a compound of formula (III):

$$X—P(R^1)_m(R^2)_n \quad (III)$$

wherein X is a halide, and $R^1$, $R^2$, m and n are as defined above for ligands having general formulae (I) and (II); and
(ii) a compound of formula (IV):

$$(R^1)_2P—N(R^3)H \quad (IV)$$

wherein $R^1$ and $R^3$ are as defined above for ligands of general formulae (I) and (II);
in the presence of an HX-acceptor.

According to a further aspect of the present invention there is provided a process for preparing a ligand having the general formula (I) or (II) which comprises reacting:
(i) a compound of formula (V):

$$X—P(R^1)_2 \quad (V)$$

wherein X is halide, and $R^1$ is as defined above for ligands of general formulae (I) and (II); and
(ii) a compound of formula (VI):

$$(R^1)_m(R^2)_nP—N(R^3)H \quad (VI)$$

wherein $R^1$, $R^2$, $R^3$, m and n are as defined above for ligands of general formulae (I) and (II);
in the presence of an HX-acceptor.

According to yet a further aspect of the present invention there is provided a ligand system prepared by reacting:
(i) a compound of formula (III):

$$X—P(R^1)_m(R^2)_n \quad (III)$$

wherein X is a halide, and $R^1$, $R^2$, m and n are as defined above for ligands (I) and (II); and
(ii) a compound of formula (IV):

$$(R^1)_2P—N(R^3)H \quad (IV)$$

wherein $R^1$ and $R^3$ are as defined above for ligands (I) and (II);
in the presence of an HX-acceptor.

According to yet a further aspect of the present invention there is provided a ligand system prepared by reacting:
(i) a compound of formula (V):

$$X—P(R^1)_2 \quad (V)$$

wherein X is halide, and $R^1$ is as defined above for ligands having the general formulae (I) and (II); and
(ii) a compound of formula (VI):

$$(R^1)_m(R^2)_nP—N(R^3)H \quad (VI)$$

wherein $R^1$, $R^2$, $R^3$, m and n are as defined above for ligands having the general formulae (I) and (II);
in the presence of an HX-acceptor.

According to the present invention there is provided a catalyst system comprising:
a) a source of chromium, molybdenum or tungsten;
b) a ligand or a ligand system as described herein; and
c) a cocatalyst.

According to another aspect of the present invention, there is provided simultaneous trimerization and tetramerization of olefinic monomers, wherein the process comprises contacting at least one olefinic monomer with the catalyst system herein at a pressure in the range of from below atmospheric to 100 barg and at a temperature in the range of from 0° C. to 200° C.

DETAILED DESCRIPTION OF THE INVENTION

As used herein, the term "trimerization" means the catalytic trimerization of an olefinic monomer to give a product composition enriched in the compound derived from the reaction of three of said olefinic monomers. The term trimerization includes the cases wherein all the olefinic monomers in the feed stream are identical as well as the cases wherein the feed stream contains two or more different olefinic monomers.

In particularly, the term "trimerization" when used in relation to the trimerization of ethylene means the trimerization of ethylene to form a $C_6$ alkene, especially 1-hexene.

The term "trimerization selectivity" when used in relation to the trimerization of ethylene means the amount of $C_6$ fraction formed within the product composition.

The term "1-hexene selectivity" when used in relation to the trimerization of ethylene means the amount of 1-hexene formed within the $C_6$ fraction of the product composition. The overall yield of 1-hexene in the trimerization of ethylene is the product of the "trimerization selectivity" multiplied by the "1-hexene selectivity".

The term "tetramerization" means the catalytic tetramerization of an olefinic monomer to give a product composition enriched in the compound derived from the reaction of four of said olefinic monomers. The term tetramerization includes the cases wherein all the olefinic monomers in the feed stream are identical as well as the cases wherein the feed stream contains two or more different olefinic monomers.

In particularly, the term "tetramerization" when used in relation to the tetramerization of ethylene means the tetramerization of ethylene to form a $C_8$ alkene, especially 1-octene.

The term "tetramerization selectivity" when used in relation to the tetramerization of ethylene means the amount of $C_8$ fraction formed within the product composition.

The term "1-octene selectivity" when used in relation to the tetramerization of ethylene means the amount of 1-octene formed within the $C_8$ fraction of the product composition. The overall yield of 1-octene in the tetramerization of ethylene is the product of the "tetramerization selectivity" multiplied by the "1-octene selectivity".

The term "hydrocarbyl" as used herein refers to a group only containing carbon and hydrogen atoms. The hydrocarbyl group may be a saturated or unsaturated, linear or branched alkyl, a non-aromatic ring or an aromatic ring. Unless otherwise stated, the preferred hydrocarbyl groups for use herein are those containing from 1 to 20 carbon atoms.

The term "substituted hydrocarbyl" as used herein refers to hydrocarbyl groups which contain one or more inert heteroatom containing functional groups. By "inert heteroatom containing functional groups" is meant that the functional groups do not interfere to any substantial degree with the trimerization and tetramerization process.

The term "heterohydrocarbyl" as used herein refers to a hydrocarbyl group wherein one or more of the carbon atoms is replaced by a heteroatom, such as Si, S, N or O. The carbon atom of the hydrocarbyl group which is replaced by a heteroatom can be either an internal carbon atom of the hydrocarbyl group or the carbon atom through which the heterohydrocarbyl group is attached, e.g. the atom which is attached to the nitrogen atom in the case of the bridging group, e.g. —N(OMe)-. The term "substituted heterohydrocarbyl" as used herein refers to heterohydrocarbyl groups which contain one or more inert heteroatom containing functional groups.

The term "aromatic" as used herein, refers to a monocyclic or polycyclic, aromatic or heteroaromatic ring having from 5 to 14 ring atoms, optionally containing from 1 to 3 heteroatoms selected from N, O and S. Preferably, the aromatic groups are monocyclic or polycyclic aromatic rings, such as cyclopentadienyl (which can also include ferrocenyl groups), phenyl, biphenyl, naphthyl or anthracenyl. Unless otherwise stated, the preferred aromatic groups are monocyclic or polycyclic aromatic rings having from 5 to 10 ring atoms, more preferred aromatic groups are monocyclic aromatic rings containing from 5 to 6 carbon atoms, such as phenyl and cyclopentadienyl, and a most preferred aromatic group is a phenyl group. The term "substituted aromatic" as used herein means that the aromatic group may be substituted with one or more substituents.

By the term "ortho-position" when used in relation to substituents on aromatic $R^1$ and/or $R^2$ groups, it is meant that the substituent is in the ortho position relative to the atom bonded to the phosphorus atom.

The ligands of the present invention have the general formulae (I) and (II) below:

$$(R^1)_2P—P(R^1)_m(R^2)_n=N(R^3) \quad (I)$$

$$P(R^1)_m(R^2)_n—P(R^1)_2=N(R^3) \quad (II)$$

wherein $R^1$, $R^2$, $R^3$, and $R^4$ are as defined above.

$R^3$ is selected from hydrogen, a hydrocarbyl group, a substituted hydrocarbyl group, a heterohydrocarbyl group, a substituted heterohydrocarbyl group, a silyl group or derivative thereof. Typically, $R^3$ is selected from hydrogen or the groups consisting of alkyl, substituted alkyl, aryl, substituted aryl, aryloxy, substituted aryloxy, alkenyl, substituted alkenyl, cycloalkyl, substituted cycloalkyl, alkoxycarbonyl, carbonyloxy, alkoxy, aminocarbonyl, carbonylamino, dialkylamino, silyl groups or derivatives thereof, and alkyl or aryl groups substituted with any of these substituents or halogen or a nitro group. More preferably $R^3$ is an alkyl, substituted alkyl (including heterocyclic substituted alkyl with at least one heteroatom, such as N or O, and alkyl groups substituted with a heteroatom or heteroatomic group), cycloalkyl, substituted cycloalkyl, substituted cyclic aryl, substituted aryl, aryloxy or substituted aryloxy group. Examples of suitable $R^3$ groups include $C_1$-$C_{15}$ alkyl groups, substituted $C_1$-$C_{15}$ alkyl groups, $C_2$-$C_{15}$ alkenyl groups, substituted $C_2$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups. Most preferred $R^3$ groups are the $C_1$-$C_{15}$ alkyl groups, which include both linear and branched alkyl groups; suitable examples include methyl, ethyl, propyl, isopropyl, butyl, isobutyl, tert-butyl, pentyl, alkyl branched pentyl groups, hexyl, alkyl branched hexyl groups, heptyl, alkyl branched heptyl groups, octyl and alkyl branched octyl groups.

Examples of suitable $=N(R^3)$ groups include $=N$(methyl), $=N$(ethyl), $=N$(propyl), $=N$(isopropyl), $=N$(butyl), $=N$(tert-butyl), $=N$(pentyl), $=N$(hexyl), $=N$(2-ethylhexyl), $=N$(cyclohexyl), $=N$(1-cyclohexylethyl), $=N$(2-methylcyclohexyl), $=N$(benzyl), $=N$(phenyl), $=N$(2-octyl), $=N$(4-methoxyphenyl), $=N$(4-tert-butylphenyl), $=N((CH_2)_3$—N-morpholine), $=N(Si(CH_3)_3)$, $=N(CH_2CH_2CH_2Si(OMe)_3))$, $=N$(decyl) and $=N$(allyl).

The substituents on the $R^1$ and/or $R^2$ groups can contain carbon atoms and/or heteroatoms. The substituents may be either polar or non-polar. Suitable substituents include hydrocarbyl groups which may be straight-chain or branched, saturated or unsaturated, aromatic or non-aromatic. The hydrocarbyl substituents may optionally contain heteroatoms such as Si, S, N or O. Suitable aromatic hydrocarbyl substituents include monocyclic and polycyclic aromatic groups, preferably having from 5 to 10 carbon atoms in the ring, such as phenyl and $C_1$-$C_4$ alkyl phenyl groups. Suitable non-aromatic hydrocarbyl substituents include linear or branched alkyl or cycloalkyl groups, preferably having from 1 to 10 carbon atoms, more preferably 1 to 4 carbon atoms.

Other suitable substituents on the $R^1$ and/or $R^2$ groups include halides such as chloride, bromide and iodide, thiol, —OH, $A^1$-O—, —S-$A^1$, —CO-$A^1$, —$NH_2$, —$NHA^1$, —$NA^1A^2$, —CO—$NA^1A^2$, —$NO_2$, $=O$, in which $A^1$ and $A^2$, independently, are non-aromatic groups preferably having from 1 to 10 carbon atoms, more preferably 1 to 4 carbon atoms, e.g. methyl, ethyl, propyl and isopropyl.

When the $R^1$ and/or $R^2$ groups of the ligand are substituted, preferred substituents are hydrocarbyl groups. Particularly preferred hydrocarbyl substituents are $C_1$-$C_4$ alkyl groups, preferably methyl, ethyl, propyl, isopropyl, butyl, isobutyl, most preferably methyl.

In one embodiment of the present invention, m is 1 and n is 1. In another embodiment m is 0 and n is 2. Typically, in the ligands of the present invention, component (b), m is 0 and n is 2.

The $R^1$ groups of the ligand are independently selected from optionally substituted aromatic groups, each bearing a polar substituent on at least one of the ortho-positions. For the avoidance of doubt, the phrase "bearing a polar substituent on at least one of the ortho-positions" means that, in the same ligand, the $R^1$ group is substituted with a polar substituent on one or both of its ortho positions.

The term "optionally substituted" in relation to the $R^1$ groups of the ligand of the present invention, which are independently selected from optionally substituted aromatic groups, each bearing a polar substituent on at least one of the ortho-positions, means that, in addition to the polar substituent on at least one of the ortho-positions, the same $R^1$ group may contain one or more other substituents.

Polar is defined by IUPAC as an entity with a permanent electric dipole moment. Therefore, as used herein, the term "polar substituents" means a substituent which incorporates a permanent electric dipole moment.

Suitable polar substituents for use herein include but are not necessarily limited to, optionally branched $C_1$-$C_{20}$ alkoxy groups, i.e. the $R^1$ and/or $R^2$ groups are substituted with a hydrocarbyl group connected through an oxygen bridging atom; optionally substituted $C_5$-$C_{14}$ aryloxy groups, i.e. the $R^1$ and/or $R^2$ groups are substituted with an optionally substituted aromatic group connected through an oxygen bridging atom; optionally branched $C_1$-$C_{20}$ alkoxy($C_1$-$C_{20}$)alkyl groups, i.e. the $R^1$ and/or $R^2$ groups are substituted with a $C_1$-$C_{20}$ hydrocarbyl group bearing a $C_1$-$C_{20}$ alkoxy group; hydroxyl; amino; (di-)$C_1$-$C_6$ alkylamino; nitro; $C_1$-$C_6$ alkylsulphonyl; $C_1$-$C_6$ alkylthio($C_1$-$C_6$)alkyl groups; sulphate; heterocyclic groups, especially with at least one N and/or O ring atom; and tosyl groups.

Examples of suitable polar substituents include methoxy, ethoxy, isopropoxy, phenoxy, decyloxy, dodecyloxy, tetradecyloxy, hexadecyloxy, octadecyloxy, eicosanoxy, pentafluorophenoxy, trimethylsiloxy, dimethylamino, methylsulphonyl, tosyl, methoxymethyl, methylthiomethyl, 1,3-oxazolyl, hydroxyl, amino, methoxymethyl, phosphino, arsino, stibino, sulphate, nitro and the like.

Preferably, the polar substituents in the $R^1$ groups are independently selected from optionally branched $C_1$-$C_{20}$ alkoxy groups, optionally substituted $C_5$-$C_{14}$ aryloxy groups, and optionally branched $C_1$-$C_{20}$ alkyl($C_1$-$C_{20}$)alkoxy groups. More preferably, the polar substituents are independently selected from optionally branched $C_1$-$C_{20}$ alkoxy groups, especially optionally branched $C_1$-$C_6$ alkoxy groups such as, for example, methoxy, ethoxy or isopropoxy of which methoxy is a particularly preferred polar substituent; alternatively, longer optionally branched $C_1$-$C_{20}$ alkoxy groups such as optionally branched $C_8$-$C_{20}$ alkoxy groups, for example decyloxy, dodecyloxy, tetradecyloxy, hexadecyloxy, octadecyloxy or eicosanoxy groups, of which eicosanoxy is preferred, may be preferred as the polar substituents in order to increase the solubility of the ligand in organic media.

In one embodiment, the $R^1$ group is independently selected from substituted or unsubstituted aromatic groups bearing an optionally branched $C_1$-$C_{20}$ alkoxy group on at least one of the ortho-positions, such as an o-anisyl group.

It is preferred that the $R^1$ groups of the ligands having the formulae (I) and (II) are the same and bear the same number and type of polar substituent(s). It is particularly preferred that each of said $R^1$ groups bears a polar substituent on only one of the two available ortho-positions.

The $R^2$ groups of the ligands having the formulae (I) and (II) are independently selected from hydrocarbyl, substituted hydrocarbyl, heterohydrocarbyl and substituted heterohydrocarbyl groups with the proviso that when the group is aromatic it does not contain a polar substituent at any of the ortho-positions. It is preferred that each of said $R^2$ groups are independently selected from substituted or unsubstituted aromatic groups, including substituted or unsubstituted heteroaromatic groups, which do not contain a polar substituent at any of the ortho-positions.

Said $R^2$ groups may be independently selected from a group comprising optionally substituted benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, tert-butyl, propenyl, propynyl, cyclopentyl, cyclohexyl, ferrocenyl and tetrahydrofuranyl groups. In another embodiment of the ligand, said $R^2$ groups may be independently selected from a group comprising optionally substituted phenyl, tolyl, biphenyl, naphthyl, thiophenyl and ethyl groups.

In a preferred embodiment of the present invention, said $R^2$ groups are independently selected from optionally substituted phenyl groups which do not contain a polar substituent at any of the ortho-positions, or alternatively, do not contain any polar substituents at all. Any polar substituent present in said $R^2$ groups may be electron donating. Said $R^2$ groups may optionally contain non-polar substituent.

IUPAC defines non-polar as an entity without a permanent electric dipole moment.

Suitable non-polar substituents may be a methyl, ethyl, propyl, butyl, isopropyl, isobutyl, tert-butyl, pentyl, hexyl, cyclopentyl, 2-methylcyclohexyl, cyclohexyl, cylopentadienyl, phenyl, biphenyl, naphthyl, tolyl, xylyl, mesityl, ethenyl, propenyl and benzyl group, or the like. Preferably, the non-polar substituent is not electron donating.

In one specific embodiment herein said $R^2$ group is an unsubstituted phenyl group.

Optionally, any of the $R^1$ and $R^2$ groups may independently be linked to one or more of each other or to the $=N(R^3)$ group to form a cyclic structure. In particular, when n is 2 then the two $R^2$ groups may optionally be linked together to form a cyclic structure incorporating the phosphorus atom.

In another embodiment of the present invention, one or both of the phosphorus atoms of the ligands of the present invention may be independently oxidised by S, Se, N or O. Typically, neither of the phosphorus atoms of the second ligand are oxidised by S, Se, N or O.

The ligands according to general formulae (I) and (II) can be prepared by a process which comprises reacting:

(i) a compound of formula (III):

wherein X is a halide, and $R^1$, $R^2$, m and n are as defined above for ligands (I) and (II); and (ii) a compound of formula (IV):

wherein $R^1$ and $R^3$ are as defined above for ligands (I) and (II); in the presence of an HX-acceptor.

Suitable HX acceptors include neopentyl lithium, n-butyl lithium, sec-butyl lithium, lithium hydride, sodium hydride, potassium hydride, triethylamine, trimethylamine, tripropylamine and the like.

The ligands according to general formulae (I) and (II) can alternatively be prepared by a process which comprises reacting:

(i) a compound of formula (V):

wherein X is a halide and $R^1$ is as defined above for general formulae (I) and (II); and (ii) a compound of formula (VI):

wherein $R^1$, $R^2$, $R^3$, m and n are as defined above for ligands of general formulae (I) and (II); in the presence of an HX acceptor.

While not wishing to be bound by theory it is believed that in the presence of an activated metal component (a), e.g. activated chromium, an equilibrium exists between ligands of the P—P=N type and ligands of the P—N—P type as shown below:

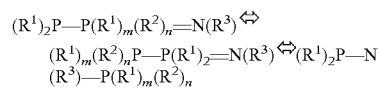

Therefore according to another aspect of the present invention there is provided a ligand system prepared by a process which comprises reacting:
(i) a compound of formula (III):

$$X—P(R^1)_m(R^2)_n \quad (III)$$

wherein X is a halide, and $R^1$, $R^2$, m and n are as defined above for ligands of general formulae (I) and (II); and
(ii) a compound of formula (IV):

$$(R^1)_2P—N(R^3)H \quad (IV)$$

wherein $R^1$ and $R^3$ are as defined above for ligands of general formulae (I) and (II); in the presence of an HX-acceptor.

There is also provided herein a ligand system prepared by a process which comprises reacting:
(i) a compound of formula (V):

$$X—P(R^1)_2 \quad (V);$$

wherein X is a halide and $R^1$ is as defined above for ligands of general formula (I) and (II); and
(ii) a compound of formula (VI):

$$(R^1)_m(R^2)_nP—N(R^3)H \quad (VI)$$

wherein $R^1$, $R^2$, $R^3$, m and n are as defined above for ligands of general formula (I) and (II);
in the presence of an HX acceptor.

Examples of ligands of the present invention include the two P—P=N forms of each of the P—N—P structures listed below: (2-methoxyphenyl)$_2$PN(methyl)P(2-methoxyphenyl)(phenyl), (2-methoxyphenyl)$_2$PN(methyl)P(phenyl)$_2$, (2-ethoxyphenyl)$_2$PN(methyl)P(2-ethoxyphenyl)(phenyl), (2-ethoxyphenyl)$_2$PN(methyl)P(phenyl)$_2$, (2-methoxyphenyl)(2-ethoxyphenyl)PN(methyl)P(2-methoxyphenyl)(phenyl), (2-methoxyphenyl)(2-ethoxyphenyl)PN(methyl)P(phenyl)$_2$, (2-isopropoxyphenyl)$_2$PN(methyl)P(2-isopropoxyphenyl)(phenyl), (2-isopropoxyphenyl)$_2$PN(methyl)P(phenyl)$_2$, (2-methoxyphenyl)$_2$PN(methyl)P(2-methoxyphenyl)(3-methoxyphenyl), (2-methoxyphenyl)$_2$PN(methyl)P(3-methoxyphenyl)$_2$, (2-methoxyphenyl)$_2$PN(methyl)P(2-methoxyphenyl)(4-methoxyphenyl), (2-methoxyphenyl)$_2$PN(methyl)P(4-methoxyphenyl)$_2$, (2-methoxyphenyl)$_2$PN(methyl)P(2-methoxyphenyl)(4-fluorophenyl), (2-methoxyphenyl)$_2$PN(methyl)P(4-fluorophenyl)$_2$, (2-methoxyphenyl)$_2$PN(methyl)P(2-ethoxyphenyl)(4-fluorophenyl), (2-methoxyphenyl)$_2$PN(methyl)P(2-methoxyphenyl)(4-dimethylamino-phenyl), (2-methoxyphenyl)$_2$PN(methyl)P(4-dimethylamino-phenyl)$_2$, (2-methoxyphenyl)$_2$PN(methyl)P(2-methoxyphenyl)(4-(4-methoxyphenyl)-phenyl), (2-methoxyphenyl)$_2$PN(methyl)P(4-(4-methoxyphenyl)-phenyl)$_2$, (2-methoxyphenyl)$_2$PN(methyl)P(2-methoxyphenyl)(4-dimethylamino-phenyl), (2-methoxyphenyl)$_2$PN(methyl)P(4-dimethylamino-phenyl)$_2$, (2-methoxyphenyl)$_2$PN(methyl)P(2-methoxyphenyl)(4-(4-methoxyphenyl)-phenyl), (2-methoxyphenyl)$_2$PN(methyl)P(4-(4-methoxyphenyl)-phenyl)$_2$, (2-methoxyphenyl)$_2$PN(methyl)P(2-methoxyphenyl)(ethyl), (2-methoxyphenyl)$_2$PN(methyl)P(ethyl)$_2$, (2-methoxyphenyl)$_2$PN(methyl)P(2-methoxyphenyl)(2-ethylphenyl), (2-methoxyphenyl)$_2$PN(methyl)P(2-ethylphenyl)$_2$, (2-methoxyphenyl)$_2$PN(methyl)P(2-methoxyphenyl)(2-naphthyl), (2-methoxyphenyl)$_2$PN(methyl)P(2-naphthyl)$_2$, (2-methoxyphenyl)$_2$PN(methyl)P(2-methoxyphenyl)(4-biphenyl), (2-methoxyphenyl)$_2$PN(methyl)P(4-biphenyl)$_2$, (2-methoxyphenyl)$_2$PN(methyl)P(2-methoxyphenyl)(4-methylphenyl), (2-methoxyphenyl)$_2$PN(methyl)P(4-methylphenyl)$_2$, (2-methoxyphenyl)$_2$PN(methyl)P(2-methoxyphenyl)(2-thiophenyl), (2-methoxyphenyl)$_2$PN(methyl)P(2-thiophenyl)$_2$, (2-methoxyphenyl)$_2$PN(methyl)P(2-methoxyphenyl)(3-methylphenyl), (2-methoxyphenyl)$_2$PN(methyl)P(3-methylphenyl)$_2$, (2-methoxyphenyl)$_2$PN(ethyl)P(2-methoxyphenyl)(phenyl), (2-methoxyphenyl)$_2$PN(ethyl)P(phenyl)$_2$, (2-methoxyphenyl)$_2$PN(propyl)P(2-methoxyphenyl)(phenyl)(2-methoxyphenyl)$_2$PN(propyl)P(phenyl)$_2$, (2-methoxyphenyl)$_2$PN(isopropyl)P(2-methoxyphenyl)(phenyl), (2-methoxyphenyl)$_2$PN(isopropyl)P(phenyl)$_2$, (2-methoxyphenyl)$_2$PN(butyl)P(2-methoxyphenyl)(phenyl), (2-methoxyphenyl)$_2$PN(butyl)P(phenyl)$_2$, (2-methoxyphenyl)$_2$PN(tert-butyl)P(2-methoxyphenyl)(phenyl), (2-methoxyphenyl)$_2$PN(tert-butyl)P(phenyl)$_2$, (2-methoxyphenyl)$_2$PN(phenyl)P(2-methoxyphenyl)(phenyl), (2-methoxyphenyl)$_2$PN(phenyl)P(phenyl)$_2$, (2-methoxyphenyl)$_2$PN(cyclohexyl)P(2-methoxyphenyl)(phenyl), (2-methoxyphenyl)$_2$PN(cyclohexyl)P(phenyl)$_2$, (2-methoxyphenyl)$_2$PN(1-cyclohexylethyl)P(2-methoxyphenyl)(phenyl), (2-methoxyphenyl)$_2$PN(1-cyclohexylethyl)P(phenyl)$_2$, (2-methoxyphenyl)$_2$PN(2-methylcyclohexyl)P(2-methoxyphenyl)(phenyl), (2-methoxyphenyl)$_2$PN(2-methylcyclohexyl)P(phenyl)$_2$, (2-methoxyphenyl)$_2$PN(decyl)P(2-methoxyphenyl)(phenyl), (2-methoxyphenyl)$_2$PN(decyl)P(phenyl)$_2$, (2-methoxyphenyl)$_2$PN(allyl)P(2-methoxyphenyl)(phenyl), (2-methoxyphenyl)$_2$PN(allyl)P(phenyl)$_2$, (2-methoxyphenyl)$_2$PN(4-methoxyphenyl)P(2-methoxyphenyl)(phenyl), (2-methoxyphenyl)$_2$PN(4-methoxyphenyl)P(phenyl)$_2$, (2-methoxyphenyl)$_2$PN(4-tert-butylphenyl)P(2-methoxyphenyl)(phenyl), (2-methoxyphenyl)$_2$PN(4-tert-butylphenyl)P(phenyl)$_2$, (2-methoxyphenyl)$_2$PN((CH$_2$)$_3$—N-morpholine)P(2-methoxyphenyl)(phenyl), (2-methoxyphenyl)$_2$PN((CH$_2$)$_3$—N-morpholine)P(phenyl)$_2$, (2-methoxyphenyl)$_2$PN(Si(CH$_3$)$_3$)P(2-methoxyphenyl)(phenyl), (2-methoxyphenyl)$_2$PN(Si(CH$_3$)$_3$)P(phenyl)$_2$, (2-methoxyphenyl)$_2$PN(benzyl)P(2-methoxyphenyl)(phenyl), (2-methoxyphenyl)$_2$PN(benzyl)P(phenyl)$_2$, (2-methoxyphenyl)$_2$PN(1-cyclohexyl-ethyl)P(2-methoxyphenyl)(phenyl), (2-methoxyphenyl)$_2$PN(1-cyclohexyl-ethyl)P(phenyl)$_2$, (2-methoxyphenyl)$_2$PN[CH$_2$CH$_2$CH$_2$Si(OMe$_3$)]P(2-methoxyphenyl)(phenyl), (2-methoxyphenyl)$_2$PN[CH$_2$CH$_2$CH$_2$Si(OMe$_3$)]P(phenyl)$_2$, (2-methoxyphenyl)$_2$PN(2-methylcyclohexyl)P(2-methoxyphenyl)(phenyl), (2-methoxyphenyl)$_2$PN(2-methylcyclohexyl)P(phenyl)$_2$, (2-eicosanoxyphenyl)$_2$PN(methyl)P(2-eicosanoxyphenyl)(phenyl), (2-eicosanoxyphenyl)$_2$PN(methyl)P(phenyl)$_2$, (2-methoxyphenyl)(2-eicosanoxyphenyl)PN(methyl)P(phenyl)$_2$, (2-methoxyphenyl)(2-eicosanoxyphenyl)PN(methyl)P(2-eicosanoxyphenyl)(phenyl), (2-eicosanoxyphenyl)$_2$PN(methyl)P(4-eicosanoxyphenyl)(phenyl), (2-methoxyphenyl)(2-eicosanoxyphenyl)PN(methyl)P(4-eicosanoxyphenyl)(phenyl), (2-eicosanoxyphenyl)$_2$PN(methyl)P(4-eicosanoxyphenyl)$_2$, (2-methoxyphenyl)(2-eicosanoxyphenyl)PN(methyl)P(4-eicosanoxyphenyl)$_2$, (2-eicosanoxyphenyl)$_2$PN(methyl)P(2-eicosanoxyphenyl)(4-eicosanoxyphenyl), (2-methoxyphenyl)(2-eicosanoxyphenyl)PN(methyl)P(2-eicosanoxyphenyl)(4-eicosanoxyphenyl), and the like.

For example, the two P—P=N forms of the (2-methoxyphenyl)$_2$PN(methyl)P(phenyl)$_2$ ligand are (2-methoxyphenyl)$_2$P—P(phenyl)$_2$=N(methyl) and (phenyl)$_2$P—P(2-methoxyphenyl)$_2$=N(methyl).

The ligands and ligand systems of the present invention can be used in a catalyst system which comprises:
(a) a source of chromium, molybdenum or tungsten;
(b) a ligand or ligand system as described herein; and
(c) a cocatalyst.

The source of chromium, molybdenum or tungsten, component (a), for the catalyst system of the present invention can include simple inorganic and organic salts of chromium, molybdenum or tungsten. Examples of simple inorganic and organic salts are halides, acetylacetonates, carboxylates, oxides, nitrates, sulfates and the like. Further sources of chromium, molybdenum or tungsten can also include co-ordination and organometallic complexes, for example chromium trichloride tris-tetrahydrofuran complex, (benzene)tricarbonylchromium, chromium hexacarbonyl, and the like. Preferably, the source of chromium, molybdenum or tungsten, component (a), for the catalyst system are selected from simple inorganic and organic salts of chromium, molybdenum or tungsten.

In one embodiment of the present invention, the source of chromium, molybdenum or tungsten, component (a), for the catalyst system is a simple inorganic or organic salt of chromium, molybdenum or tungsten, which is soluble in a solvent such as those disclosed in U.S. Pat. No. 7,141,633 which is herein incorporated by reference in its entirety.

The source of chromium, molybdenum or tungsten can also include a mixture of any combination of simple inorganic salts, simple organic salts, co-ordination complexes and organometallic complexes.

In a preferred embodiment herein, component (a) is a source of chromium, particularly chromium (III).

Preferred sources of chromium for use herein are simple inorganic and organic salts of chromium and co-ordination or organometallic complexes of chromium. More preferred sources of chromium for use herein are the simple inorganic and organic salts of chromium, such as salts of carboxylic acids, preferably salts of alkanoic acids containing 1 to 30 carbon atoms, salts of aliphatic-β-diketones and salts of β-ketoesters (e.g. chromium (III) 2-ethylhexanoate, chromium (III) octanoate and chromium (III) acetylacetonate), and halide salts of chromium, such as chromium trichloride, chromium trichloride tris-tetrahydrofuran complex, chromium tribromide, chromium trifluoride, and chromium tri-iodide. Specific examples of preferred sources of chromium for use herein are chromium (III) acetylacetonate, also called chromium tris(2,4-pentanedionate), $Cr(acac)_3$, chromium trichloride, $CrCl_3$, and chromium trichloride tris-tetrahydrofuran complex, $CrCl_3(THF)_3$.

The cocatalyst, component (c), may in principle be any compound or mixture of compounds that generates an active catalyst system with the source of chromium, molybdenum or tungsten, component (a), and the ligand, component (b).

Compounds which are suitable for use as a cocatalyst include organoaluminium compounds, organoboron compounds, organic salts, such as methyllithium and methylmagnesium bromide and inorganic acids and salts, such as tetrafluoroboric acid etherate, silver tetrafluoroborate, sodium hexafluoroantimonate and the like.

Particularly preferred cocatalysts are organoaluminium compounds. Suitable organoaluminium compounds for use herein are those having the formula $AlR^4_3$, wherein each $R^4$ group is independently selected from $C_1-C_{30}$ alkyl (preferably $C_1-C_{12}$ alkyl), oxygen containing moieties or halides, and compounds such as $LiAlH_4$ and the like. Non-limiting examples of suitable organoaluminium compounds include trimethylaluminium (TMA), triethylaluminium (TEA), tri-n-butyl aluminium, tri-isobutylaluminium (TIBA), tri-n-octylaluminium, methylaluminium dichloride, ethylaluminium dichloride, dimethylaluminium chloride, diethylaluminium chloride and aluminoxanes (also called alumoxanes). Mixtures of organoaluminium compounds are also suitable for use herein.

In a preferred embodiment herein, the cocatalyst is an aluminoxane cocatalyst. These aluminoxane cocatalysts may comprise any aluminoxane compound or a mixture of aluminoxane compounds. Aluminoxanes may be prepared by the controlled addition of water to an alkylaluminium compound, such as those mentioned above, or are available commercially. Non-limiting examples of suitable aluminoxanes include methyl aluminoxane (MAO), modified methyl aluminoxane (MMAO), tetraisobutyl dialuminoxane (TIBAO), tetra-n-butyl dialuminoxane and tetra-n-octyl dialuminoxane. In this context it should be noted that the term "aluminoxane" as used within this specification includes commercially available aluminoxanes, which are derived from the corresponding trialkylaluminium by addition of water and which may contain from 2 to 15% wt., typically about 5% wt., but optionally about 10% wt., of aluminium.

Other suitable co-catalysts include those mentioned in U.S. Pat. No. 7,141,633, U.S. Published Patent Applications Nos. 2006/0128910, 2006/0173226, 2006/0211903, and 2006/0229480, which are incorporated herein in their entirety by reference.

The quantity of cocatalyst in the catalyst system the present invention is typically enough to provide a ratio in the range from 0.1 to 20,000, preferably from 1 to 2000, more preferably 1 to 1000, most preferably 1 to 500, aluminium or boron atoms per atom of chromium, molybdenum or tungsten.

The catalyst system of the present invention may independently comprise more than one ligand as defined above.

The amount of chromium, molybdenum or tungsten, namely component (a), and the amount of ligand, component (b), can be present in the system in a molar ratio in the range of from 100:1 to 1:100, preferably from 10:1 to 1:10. More preferably, the chromium, molybdenum or tungsten, component (a), and the ligand, component (b), are present in a molar ratio in the range of from 3:1 to 1:3. Most preferably the amount of component (a) and the amount of component (b) are present in a molar ratio of from 1:0.9 to 1:1.1.

The three catalyst components of the catalyst system, (a), (b) and (c), may be added together simultaneously or sequentially in any order so as to provide an active catalyst. The three catalyst components of the catalyst system, (a), (b) and (c), may be contacted in the presence of any suitable solvent. Suitable solvents are known to those skilled in the art, suitable solvents may include any inert solvent that does not react with the co-catalyst component, such as saturated aliphatic, unsaturated aliphatic, aromatic, halogenated hydrocarbons and ionic liquids. Typical solvents include, but are not limited to, benzene, toluene, xylene, ethylbenzene, cumene, propane, butane, pentane, heptane, decane, dodecane, tetradecane, methylcyclohexane, methylcyclopentane, cyclohexane, 1-hexene, 1-octene and the like. Other examples of suitable solvents are those disclosed in WO 02/04119, such as hydrocarbon solvents and polar solvents such as diethyl ether, tetrahydrofuran, acetonitrile and the like.

In one embodiment of the present invention, the catalyst system is formed by adding the co-catalyst component, (c), to a catalyst precursor composition comprising components (a) and (b).

The catalyst system of the present invention may be prepared either in the presence (i.e. "in-situ") or absence of the olefinic monomer. The three catalyst components of the catalyst system, (a), (b) and (c), may be combined fully in the absence of the olefinic monomer, or the olefinic monomer may be included prior to contacting the components of the catalyst system, simultaneously with the components of the catalyst system or at any point in the process of contacting the components of the catalyst.

The three components of the catalyst system, (a), (b) and (c), may be combined at a temperature in the range of from −100 to 200° C., preferably 0 to 150° C., more preferably 20 to 100° C.

The catalyst system of the present invention may be unsupported or supported on a support material. Examples of suitable support materials can be found in U.S. Pat. No. 7,141,633, U.S. Published Patent Applications Nos. 2006/0128910, 2006/0173226, 2006/0211903, and 2006/0229480, which are incorporated herein in their entirety by reference.

The olefinic monomers suitable for use in the trimerization and tetramerization process of the present invention can be any olefinic monomers, which can be converted into a trimer or tetramer. Suitable olefinic monomers include, but are not necessarily limited to, ethylene, propylene, optionally branched $C_4$-$C_{24}$, preferably $C_4$-$C_{20}$, α-olefins, optionally branched $C_4$-$C_{24}$, preferably $C_4$-$C_{20}$, internal olefins, optionally branched $C_4$-$C_{24}$, preferably $C_4$-$C_{20}$, vinylidene olefins, optionally branched $C_4$-$C_{24}$, preferably $C_4$-$C_{20}$, cyclic olefins and optionally branched $C_4$-$C_{24}$, preferably $C_4$-$C_{20}$, dienes, as well as optionally branched $C_4$-$C_{24}$, preferably $C_4$-$C_{20}$, functionalized olefins. Examples of suitable olefinic monomers include, but are not necessarily limited to, linear α-olefins, such as ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene and 1-eicosene; branched α-olefins such as 4-methylpent-1-ene and 2-ethyl-1-hexene; linear and branched internal-olefins such as 2-butene; styrene; cyclohexene; norbornene and the like.

Mixtures of olefinic monomers can also be used in the process of the present invention.

Preferred olefinic monomers for use in the trimerization and tetramerization process of the present invention are propylene and ethylene. Especially preferred is ethylene.

The catalyst system and process of the present invention are particularly useful for the simultaneous trimerization and tetramerization of ethylene to 1-hexene and 1-octene.

The simultaneous trimerization and tetramerization reaction can be performed in solution phase, slurry phase, gas phase or bulk phase.

When the simultaneous trimerization and tetramerization is performed in solution or slurry phase, a diluent or solvent, which is substantially inert under trimerization and tetramerization conditions may be employed. Suitable diluents or solvents are aliphatic and aromatic hydrocarbons, halogenated hydrocarbons and olefins which are substantially inert under trimerization and tetramerization conditions may be employed, such as those disclosed in U.S. Pat. No. 7,141,633, U.S. Published Patent Applications Nos. 2006/0128910, 2006/0173226, 2006/0211903, and 2006/0229480, which are incorporated herein in their entirety by reference.

The trimerization and tetramerization process of the present invention may be performed in any one of a number of suitable reactors, which are well known to one skilled in the art. Typically the trimerization and tetramerization process of the present invention is carried out in a batch, semi-batch or continuous mode.

The simultaneous trimerization and tetramerization process of the present invention may be carried out under the following range of reaction conditions. Typically, the temperature will be in the range from about 0° C. to about 200° C., preferably from about 10° C. to about 150° C., more preferably from about 40° C. to about 150° C., even more preferably from about 70° C. to about 150° C. The process of present invention may also conveniently be performed at temperature range of from about 20° C. to about 120° C. However, it may be commercially desirable to perform the process of the present invention at an elevated temperature, therefore, the process of the present invention is highly suitable to be applied at a temperature in the range of from about 70° C. to about 100° C. The pressure range under which the process of the present invention may be performed is typically in the range of from below atmospheric pressure to about 100 barg. Preferably, the pressure will be in the range from about 0.1 to about 80 barg, more preferably from about 0.5 to about 70 barg, especially in the range of from about 1 to about 60 barg. Temperatures and pressures outside those stated above may also be employed, however, the reaction product will either have an excess of heavy and/or solid by-products or an insignificant amount of the trimer or tetramer.

By varying the temperature and pressure it is possible for the ratio of trimers and tetramers produced in the process of the present invention to be varied. The process of the present invention can be used as a tunable process for the trimerization and tetramerization of olefinic monomers. By the term "tunable" as used herein, it is meant that by varying the reaction conditions of the process of the present invention, the amount of trimers and tetramers in the product composition produced by the process of the present invention may be varied. This may be useful for a tunable, continuous or semi-continuous, process for the trimerization and tetramerization of olefinic monomers, wherein the product composition can be changed (e.g. from producing a higher proportion of trimers to a higher proportion of tetramers, or vice-versa,) by changing the reactor conditions without having to interrupt the olefinic monomer feed or the trimerization and tetramerization product flow. In particular, this may be especially useful for a tunable, continuous or semi-continuous, process for the trimerization and tetramerization of ethylene, wherein the product composition can be changed (e.g. from producing a higher proportion of 1-hexene to a higher proportion of 1-octene, or vice-versa) by changing the reactor conditions without having to interrupt the olefinic monomer feed or the trimerization and tetramerization product flow.

In one embodiment of the present invention, there is a process for the trimerization and tetramerization of olefinic monomers, wherein the process comprises contacting at least one olefinic monomer under trimerization and tetramerization reaction conditions with a catalyst system of the present invention, wherein the process is a continuous or semi-continuous process and the reaction conditions are varied during the process. Variation of the reaction conditions can be performed to make continual adjustments to a process to ensure a consistent product slate or can be performed to a process to change the product slate produced. A preferred version of this embodiment is a process for the trimerization and tetramerization of ethylene, wherein the process comprises contacting ethylene with a catalyst system of the present invention, wherein the process is a continuous or semi-continuous process and the reaction conditions are varied during the process.

Separation of the products, reactant and catalyst can be performed by any technique known to one skilled in the art, such as distillation, filtration, centrifugation, liquid/liquid separation, extraction, etc.

Further details regarding reactors, solvents, separation techniques, and the like, can be found in U.S. Pat. No. 7,141,633 which is herein incorporated by reference.

The use of the process of the present invention for the catalytic trimerization and tetramerization of olefinic monomers provides a simplified method of producing trimers and tetramers of the olefinic monomer with reduced formation of by-products compared with equivalent trimerization and tetramerization processes. In particular, the use of the process of the present invention for the catalytic trimerization and tetramerization of ethylene to 1-hexene and 1-octene provides a process with very high selectivity for 1-hexene and 1-octene over all the other products formed in the $C_6$ and $C_8$ fractions respectively and with reduced formation of by-products compared with equivalent trimerization and tetramerization processes.

The overall yield of 1-hexene and 1-octene in the process for the trimerization and tetramerization of ethylene of the present invention depends upon the reaction conditions employed.

Typically, the trimerization and tetramerization selectivity (i.e. the amount of trimers and tetramers of the olefinic monomers in the overall product composition) of the process of the present invention is at least 65% wt, preferably at least 70% wt, more preferably at least 75% wt, of the overall product composition. The trimerization and tetramerization selectivity for the trimerization and tetramerization of ethylene (i.e. the amount of $C_6$ and $C_8$ fraction in the overall product composition) using the process of the present invention is at least 60% wt, preferably at least 70% wt, more preferably at least 80% wt, of the overall product composition.

The amount of 1-hexene produced by the trimerization and tetramerization of ethylene using the process of the present invention is typically in the range of from 10% wt to 90% wt, preferably from 11% wt to 85% wt, more preferably from 12% wt to 80% wt, of the overall product composition. The amount of 1-octene produced by the trimerization and tetramerization of ethylene using the process of the present invention is typically in the range of from 10% wt to 90% wt, preferably from 11% wt to 85% wt, more preferably from 12% wt to 80% wt, of the overall product composition.

The 1-hexene selectivity (i.e. the amount of 1-hexene present in the $C_6$ fraction of the product composition) in the trimerization and tetramerization of ethylene using the process of the present invention is preferably at least 85% wt, more preferably at least 90% wt, most preferably at least 92% wt of the $C_6$ fraction of the product composition.

The 1-octene selectivity (i.e. the amount of 1-octene present in the $C_8$ fraction of the product composition) in the trimerization and tetramerization of ethylene using the process of the present invention is preferably at least 85% wt, more preferably at least 90% wt, most preferably at least 92% wt of the $C_8$ fraction of the product composition.

The amount of solids produced in the trimerization and tetramerization of ethylene using the process of the present invention is typically at most about 5% wt. Lower levels of solid olefin waxes and polyethylene produced in the trimerization and tetramerization of ethylene are desirable in commercial operations as this can reduce the amount of fouling of the reactor equipment, reduce the amount of waste by-products and reduce the amount of operational "downtime" due to maintenance and cleaning of the reactor equipment.

The amount of $C_{10}$ produced in the trimerization and tetramerization of ethylene using the process of the present invention is typically at most about 10% wt.

The amount of $C_{12}$-$C_{14}$ produced in the trimerization and tetramerization of ethylene using the process of the present invention is typically at most about 10% wt.

In one embodiment of the present invention, the olefinic product composition of the trimerization and tetramerization of ethylene using the process of the present invention typically comprises a combined total content of 1-hexene and 1-octene of at least 70% wt of the overall product composition, wherein the 1-hexene content is at least 10% wt of the overall product composition, the 1-hexene selectivity is at least 90% wt of the $C_6$ fraction of the product composition, the 1-octene content is at least 10% wt of the overall product composition, the 1-octene selectivity is at least 90% wt of the $C_8$ fraction of the product composition, and the amount of solids produced is at most about 5% wt of the overall product composition.

In another embodiment of the present invention, the olefinic product composition of the trimerization and tetramerization of ethylene using the process of the present invention comprises a total content of compounds other than 1-hexene and 1-octene of at most 40% wt of the overall product composition, preferably at most 30% wt and more preferably at most 20% wt, wherein the 1-hexene content is at least 10% wt of the overall product composition, the 1-hexene selectivity is at least 90% wt of the $C_6$ fraction of the product composition, the 1-octene content is at least 10% wt of the overall product composition, the 1-octene selectivity is at least 90% wt of the $C_8$ fraction of the product composition, and the amount of solids produced is at most about 5% wt of the overall product composition.

The process of the present invention is illustrated by the following non-limiting examples.

EXAMPLES

General Procedures and Characterisation

All chemicals used in preparations were purchased from Aldrich and used without further purification unless mentioned otherwise.

All the operations with the catalyst systems were carried out under nitrogen atmosphere. All solvents used were dried using standard procedures. Anhydrous toluene (99.8% purity) was dried over 4 Å molecular sieves (final water content of about 3 ppm). Anhydrous heptane (99.8% purity) was dried by passage over 4 Å molecular sieves (final water content of about 1 ppm).

Ethylene (99.5% purity) was purified over a column containing 4 Å molecular sieves and BTS catalyst (BASF) in order to reduce water and oxygen content to <1 ppm.

The oligomers obtained were characterised by Gas Chromatography (GC), in order to evaluate oligomer distribution using a HP 5890 series II apparatus and the following chromatographic conditions:

Column: HP-1 (cross-linked methyl siloxane), film thickness=0.25 μm, internal diameter=0.25 mm, length 60 m (by Hewlett Packard); injection temperature: 325° C.; detection temperature: 325° C.; initial temperature: 40° C. for 10 minutes; temperature programme rate: 10.0° C./minute; final temperature: 325° C. for 41.5 minutes; internal standard: n-hexylbenzene. The yields of the $C_4$-$C_{30}$ olefins were obtained from the GC analysis.

The term "trimerization selectivity" when used in relation to the trimerization of ethylene to 1-hexene means the amount of $C_6$-fraction formed within the product composition, as determined by GC.

The term "tetramerization selectivity" when used in relation to the tetramerization of ethylene to 1-octene means the amount of $C_8$-fraction formed within the product composition, as determined by GC.

The term "1-hexene selectivity" when used in relation to the trimerization of ethylene to 1-hexene means the amount of 1-hexene formed within the $C_6$-fraction of the product composition, as determined by GC. The overall yield of 1-hexene in the trimerization of ethylene is the product of the "trimerization selectivity" multiplied by the "1-hexene selectivity".

The term "1-octene selectivity" when used in relation to the tetramerization of ethylene to 1-octene means the amount of 1-octene formed within the $C_8$-fraction of the product composition, as determined by GC. The overall yield of 1-octene in the tetramerization of ethylene is the product of the "tetramerization selectivity" multiplied by the "1-octene selectivity".

The amount of "solids", mainly consisting of heavy wax and polyethylene, has been determined by weighing, after its isolation from the reactor wall and appendages, followed by washing with toluene on a glass filter (P3) and by vacuum drying.

The amount of "total product" is the sum of the amount of largely olefinic product derived from GC analysis and the amount of solids.

The NMR data was obtained at room temperature with a Varian 300 MHz or 400 MHz apparatus.

Catalyst Systems

The catalyst compositions of the present invention were prepared from catalyst precursor compositions containing ligands B, C, D, E, F and G and a chromium source, these components are described below.

Chromium Source

Chromium tris(2,4-pentanedionate), also called chromium tris(acetylacetonate), i.e. $Cr(acac)_3$, was used as the chromium source in the simultaneous tri- and tetramerization reactions of ethylene.

Ligand Composition E

The reaction product between $(2\text{-methoxyphenyl})_2PNH$ (methyl) and $(phenyl)_2PCl$ (ligand component E) was prepared by the following method.

Under a nitrogen atmosphere 1.015 g (3.62 mmol) $(2\text{-methoxyphenyl})_2PCl$ in was added to 10 ml methylamine (2M in THF) in 50 ml pentane. The resulting mixture was stirred overnight at room temperature. The precipitate was removed by centrifugation. The solvents were removed from the resulting solution under vacuum. Washing with pentane yielded 0.85 g (3.09 mmol; (84%)) $(2\text{-methoxyphenyl})_2PNH$ (methyl) as a white solid. $^{31}P$-NMR (in $C_6D_6$) signal at δ 31.6.

Under a nitrogen atmosphere, 70 mg (0.90 mmol) of neopentyl lithium was slowly added to 235 mg (0.85 mmol) of $(2\text{-methoxyphenyl})_2PNH(methyl)$ in 55 ml dry toluene. To the resulting mixture 187 mg (0.85 mmol) $(phenyl)_2PCl$ in 5 ml toluene was slowly added. The mixture was stirred overnight at room temperature. To the mixture 25 ml of pentane was added. The precipitate was removed by centrifugation. The solvent was removed under vacuum and the resulting precipitate was washed with pentane. The product was isolated as a white solid. $^{31}P$-NMR (in $C_6D_6$) signals at δ 70.4 and 57.9 ($J_{PP}$=289 Hz).

According to $^{31}P$-NMR the product consisted at least predominantly of a P—P=N(methyl) structure with on one P atom two phenyl groups and on the other P atom two 2-methoxyphenyl groups, either $(phenyl)_2P(2\text{-methoxyphenyl})_2PN$(methyl) or $(2\text{-methoxyphenyl})_2P(phenyl)_2PN(methyl)$.

Upon complexation of a Pd[II] compound, $PdCl_2$[cyclooctadiene], by this ligand composition E with the P—P=N (methyl) structure isomerization to the P—N(methyl)-P structure, i.e. $(phenyl)_2PN(methyl)P(2\text{-methoxyphenyl})_2$, can be evidenced by $^{31}P$ NMR (by analogy to NMR and X-ray diffraction analysis by P. J. Dyson, et al., Eur. J. Inorg. Chem. 2004, 530 and P. J. Dyson et al., Inorganica Chimica Acta, 359, (2006), 2635-2643). It is assumed that a similar mechanism applies to the formation of chromium complexes. This can not be evidenced by NMR spectroscopy, due to the paramagnetic character of the chromium compounds.

Ligand Composition B (Comparative)

The $(2\text{-methoxyphenyl})_2PN(CH_3)P(2\text{-methoxyphenyl})_2$ ligand was prepared by first forming a solution of 1.59 g (5 mmol) $(2\text{-methoxyphenyl})_2PNEt_2$ in 20 ml diethyl ether. To this solution 10 ml of a 1 M HCl solution in diethyl ether (10 mmol HCl) was added under an inert atmosphere at room temperature. The suspension thus formed was stirred overnight. The diethyl ether was removed from the product under vacuum and 20 ml of dry toluene was added. The resulting solution was filtered and the toluene was removed from the filtrate under vacuum to yield a white solid $(2\text{-methoxyphenyl})_2PCl$ product.

A solution of 0.51 g (5 mmol) of triethylamine in 20 ml of dry dichloromethane was added to the $(2\text{-methoxyphenyl})_2PCl$ product. To the resulting mixture, 1.25 ml of a 2 M $H_2NMe$ solution in THF (2.5 mmol) was added and allowed to stir overnight. The solvents were removed from the resulting solution in vacuo and 20 ml of dry toluene was added. The mixture was then filtered.

The toluene was removed from the filtrate under vacuum, and 10 ml of methanol was added to the residue to produce a suspension, which was filtered once more, to leave the solid white $(2\text{-methoxyphenyl})_2PN(CH_3)P(2\text{-methoxyphenyl})_2$ product which was isolated.

Ligand Composition C (Comparative)

The $(phenyl)_2PN(isopropyl)P(phenyl)_2$ ligand was prepared by the following method. At 0° C., under a nitrogen atmosphere, 15 ml triethylamine was added to 6.3 g $(phenyl)_2PCl$ in 80 ml of dry dichloromethane. To the resulting mixture, 0.844 g isopropylamine was added and allowed to stir overnight at room temperature. The solvents were removed from the resulting solution in-vacuo and 50 ml of dry toluene was added. The mixture was then filtered over a small layer of silica. The toluene was removed from the filtrate under vacuum, $(phenyl)_2PN(isopropyl)P(phenyl)_2$ product was isolated as a white solid. Crystallization from ethanol yielded $(phenyl)_2PN(isopropyl)P(phenyl)_2$ as white crystals.

Ligand Composition D (Comparative)

The $(phenyl)_2PN(isopropyl)P(2\text{-methoxyphenyl})_2$ ligand was prepared by the following method.

Under a nitrogen atmosphere, 12 ml triethylamine was added to 3.39 g isopropylamine in 10 ml dry toluene. To the resulting mixture, 5.15 ml $(phenyl)_2PCl$ was slowly added and allowed to stir overnight at room temperature. The precipitate was removed by filtration. The solvents were removed from the resulting solution in vacuo. To the evaporation residue pentane was added and subsequently the solvent was removed in vacuo from the pentane solution, yielding $(phenyl)_2PNH(isopropyl)$ as a colourless oil, which crystallized on standing at room temperature.

Under a nitrogen atmosphere, 3 ml triethyl amine was added to 0.9 g of the isolated $(phenyl)_2PNH(isopropyl)$ in 5 ml of dry dichloromethane. To the resulting mixture, 1.1 g $(2\text{-methoxyphenyl})_2PCl$ was added and allowed to stir for a week at room temperature. To the resulting reaction mixture 5-10 ml of dry toluene was added. The precipitate was removed by centrifugation. The solvents were removed from the resulting solution in vacuo. The resulting mixture was first washed with pentane and thereupon stirred with methanol yielding a white solid. The white solid was washed with pentane and dried in vacuo. Yield 0.7 g of $(phenyl)_2PN(isopropyl)P(2\text{-methoxyphenyl})_2$. $^{31}P$-NMR (in $C_6D_6$) broad signals δ 55.9 and 24.8.

Ligand Composition F

The reaction product of $(2\text{-methoxyphenyl})_2PNH(methyl)$ and $(cyclohexyl)_2PCl$ Under a nitrogen atmosphere, 38 mg (0.404 mmol) of $Me_3SiCH_2Li$ was slowly added to 101 mg (0.367 mmol) of (2-methoxyphenyl)$_2$PNH(methyl) in 15 ml dry toluene. To the resulting mixture 95 mg (0.408 mmol) (cyclohexyl)$_2$PCl (Aldrich) in 5 ml toluene was slowly added. The mixture was stirred for 2 hours at room temperature. To the mixture 5 ml hexane was added. The precipitate was removed by centrifugation. The solvent was removed under vacuum. The resulting sticky material was extracted with 10-15 ml hexane. Cooling this hexane solution to −20° C. resulted in the isolation of the product as a white solid. $^{31}$P-NMR (in d$_8$-toluene) signals at δ 90.4 and 49.5 (J$_{PP}$=247 Hz). According to $^{31}$P-NMR the product consisted at least predominantly of a P—P=N(methyl) structure with on one P atom two cyclohexyl groups and on the other P atom two 2-methoxyphenyl groups, either (cyclohexyl)$_2$P(2-methoxyphenyl)$_2$PN(methyl) or (2-methoxyphenyl)$_2$P(cyclohexyl)$_2$PN(methyl) (see Scheme 1).

Scheme 1

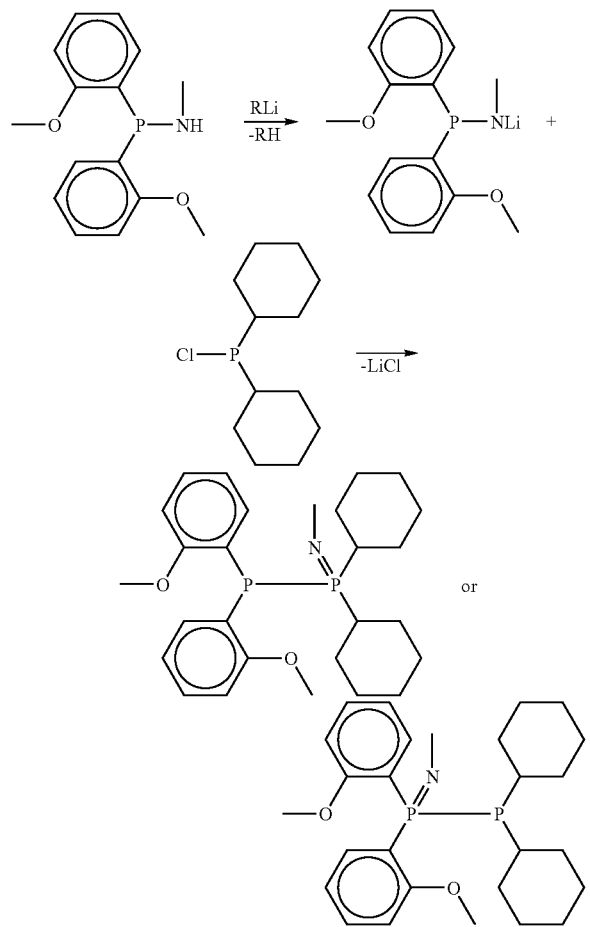

Ligand Composition G (Comparative)

The reaction product of (2-methoxyphenyl)$_2$PNH(isopropyl) and (2-methoxyphenyl)$_2$PCl (ligand composition G) was prepared as follows.

Under a nitrogen atmosphere, 3 ml triethylamine was added to 1.5 ml isopropylamine (17.6 mmol) in 5 ml dry toluene. To the resulting mixture, 2.2 g (7.84 mmol) (2-methoxyphenyl)$_2$PCl in 20 ml toluene was slowly added and allowed to stir overnight at room temperature. The precipitate was removed by centrifugation. The solvents were removed from the resulting solution in vacuo. Washing with pentane yielded (2-methoxyphenyl)$_2$PNH(isopropyl) as a white solid. $^{31}$P-NMR (in C$_6$D$_6$) δ 21.8.

Under a nitrogen atmosphere, 80 mg (1.0 mmol) of neopentyl lithium was slowly added to 300 mg (0.99 mmol) of (2-methoxyphenyl)$_2$PNH(isopropyl) in 30 ml dry toluene. To the resulting mixture 277 mg (0.99 mmol) (2-methoxyphenyl)$_2$PCl was slowly added. The mixture was stirred overnight at room temperature. The precipitate was removed by centrifugation. The solvent was removed in vacuo. The residue was washed with pentane. The product has according to $^{31}$P-NMR at least predominantly the P—P=N(isopropyl) structure, i.e. (2-methoxyphenyl)$_2$P(2-methoxyphenyl)$_2$PN (isopropyl), and was used without further purification. $^{31}$P-NMR (in C$_6$D$_6$) δ 0.0 and −35.4 (J$_{PP}$=258 Hz).

Co-Catalyst

The co-catalyst used in the experiments below was:
methyl aluminoxane (MAO) in toluene, [Al]=5.20% wt, supplied by Crompton GmbH, Bergkamen, Germany;

Examples 1-8

Catalyst System Preparation for Simultaneous Trimerization and Tetramerization in a Batch Autoclave In a Braun MB 200-G dry box chromium tris(acetylacetonate) (typically 30 μmol) and the amount of ligand component B, C, D, E, F or G as indicated in Table 1, were placed in a glass bottle, to which dry toluene (typically 4 g) was added to obtain the catalyst precursor solution. Finally the bottle was sealed with a septum cap.

These catalyst precursor solutions (the chromium tris (acetylacetonate) solutions are introduced as catalyst precursor solution which is to be activated by the pre-dosed MAO in-situ in the autoclave), or part of these solutions, were used in the simultaneous tri- and tetramerization reaction of ethylene.

Simultaneous Trimerization and Tetramerization Reactions of Ethylene in a 1.0-Liter Batch Autoclave Simultaneous tri- and tetramerization experiments were performed in a 1.0-liter steel autoclave equipped with jacket cooling with a heating/cooling bath (ex. Julabo, model ATS-2) and a turbine/gas stirrer and baffles.

The reactor was scavenged by introducing 250 ml toluene, MAO (0.6 g solution) and subsequent stirring at 70° C. under nitrogen pressure of 0.4-0.5 MPa for 30 min. The reactor contents were discharged via a tap in the base of the autoclave. The reactor was evacuated to about 0.4 kPa and loaded with approximately 250 ml toluene (or heptane), heated to 40° C. and pressurised with ethylene to 15 barg or as indicated in Table 1.

Whilst stirring, a MAO-solution (typically an intake of 3.12 g, 6 mmol Al) was added to the reactor with the aid of toluene to attain an Al/Cr atomic ratio of 200 (typically, the total volume injected was about 25 ml: the MAO-solution diluted with toluene to 8 ml was injected and the injector system was rinsed twice with 8 ml toluene) and the stirring at 800 rpm was continued for 30 minutes.

The Cr-catalyst precursor system (typically 30 μmol on Cr intake), prepared as described above, was introduced into the stirred reactor using an injection system with the aid of toluene (the total volume injected was about 25 ml: the catalyst solution diluted with toluene to 8 ml was injected and the injector system was rinsed twice with 8 ml toluene). The initial loading of the reactor was about 300 ml of largely toluene.

The addition of the catalyst system resulted, after an induction period of some 5 minutes, in an exotherm (generally some 5-10° C.), which generally reached a maximum within 1 minute and was followed by establishment of the temperature of 40° C. and the pressure of 15 barg, unless indicated differently in Table 1.

After consuming the desired volume of ethylene, the simultaneous tri- and tetramerization was stopped by rapid cooling to room temperature (in about 5 minutes), followed by venting of the ethylene, decanting the product mixture into a collection bottle using a tap in the base of the autoclave. Exposure of the mixture to air resulted in rapid deactivation of the catalyst.

After addition of n-hexylbenzene (0.5-3.5 g) as internal standard to the crude product, the amount of the $C_4$-$C_{30}$ olefins and purity of $C_6$, $C_8$ and $C_{10}$ olefins was determined by gas chromatography. The experimental data is reported in Table 1.

In the case of experiments under 30 or 50 barg of ethylene pressure a similarly equipped 0.5-liter steel autoclave has been used, loaded (similarly to the above-described procedure for the 1.0-liter autoclave) with 150 ml of toluene, a MAO-solution and a Cr-catalyst system. The amounts of the Cr-catalyst system, MAO-solution, solvent and ethylene consumption were typically half of those used in the corresponding 1.0-liter experiments to maintain the same Al/Cr atomic ratio (of about 200) and final alpha olefin concentration as much as practicable.

The experimental data is provided in Table 1 below.

TABLE 1

| Example | Cr (μmol) | Ligand ($mol_{lig}$)/($mol_{Cr}$) | Co-Catalyst | Temperature (° C.) | Pressure (barg) | Time (min) | TOF (TON)‡ | $C_6$ (% wt) | 1-$C_6$* (% wt) |
|---|---|---|---|---|---|---|---|---|---|
| 1 | 30 | E (1.1) | MAO | 70 ## | 15 | 25 | 315 (131) | 65.2 | 97.0 |
| 2 | 15 | E (1.1) | MAO | 70 ## | 30 | 25 | 772 (322) | 57.0 | 96.2 |
| 3 | 3 | E (1.1) | MAO | 100 | 50 | 47 | 867 (679) | 65.9 | 97.0 |
| 4 | 15 | F (1.2) | MAO | 70 ## | 30 | 27 | 529 (238) | 82.9 | 98.7 |
| 5# | 16 | G (1.5) | MAO | 70 | 30 | 20 | 5 (2) | 82.5 | 100.0 |
| 6# | 15 | D (1.1) | MAO | 80 | 30 | 12 | 391 (78) | 76.6 | 98.2 |
| 7# | 15 | C (1.1) | MAO | 80 | 30 | 30 | 26 (13) | 20.3 | 92.8 |
| 8# | 15 | B (1.1) | MAO | 70 ## | 30 | 36 | 705 (423) | 85.0 | 97.5 |

| Example | $C_8$ (% wt) | 1-$C_8$** (% wt) | $C_{10}$† (% wt) | $C_{12}$-$C_{14}$† (% wt) | Solids (% wt) | Total Product (g) | 1-$C_6$ + 1-$C_8$ on Total Product (% wt) |
|---|---|---|---|---|---|---|---|
| 1 | 25.1 | 98.4 | 5.5 | 3.7 | <0.1 | 109.1 | 88.0 |
| 2 | 32.1 | 98.1 | 5.0 | 4.9 | <0.1 | 134.7 | 86.3 |
| 3 | 28.8 | 98.3 | 2.8 | 2.0 | 5.7 | 56.4 | 92.2 |
| 4 | 3.1 | 97.5 | 12.4 | 0.9 | <0.7 | 101.1 | 84.9 |
| 5# | 3.6 | 93.0 | 3.0 | 3.1 | 7.2 | 0.7 | 85.8 |
| 6# | 12.2 | 97.6 | 8.1 | 1.9 | 0.4 | 32.8 | 87.1 |
| 7# | 25.9 | 94.4 | 2.3 †† | 3.7 | 47.4 | 5.5 | 43.3 |
| 8# | 4.1 | 99.8 | 10.0 | 0.9 | 0.02 | 177.6 | 87.0 |

Comparative example.
‡Turnover frequency (TOF) in hourly kmol converted ethylene/mol catalyst(kmol/mol·h); turnover number (TON) in kmol converted ethylene/mol catalyst(kmol/mol).
*% of 1-hexene by weight of the $C_6$ portion of the product composition.
**% of 1-octene by weight of the $C_8$ portion of the product composition.
†Predominantly branched and/or internal olefins, unless indicated differently.
††About 50% of 1-decene by weight of the $C_{10}$ portion of the product composition.
During 10 minutes at 40° C.
$C_6$ Hydrocarbons containing 6 carbon atoms.
1-$C_6$ 1-hexene.
$C_8$ Hydrocarbons containing 8 carbon atoms.
1-$C_8$ 1-octene.
$C_{10}$ Hydrocarbons containing 10 carbon atoms.
$C_{12}$-$C_{14}$ Hydrocarbons containing 12 and/or 14 carbon atoms.
Solids The amount of wax and polyethylene isolated by filtration.
Total product The amount of $C_4$-$C_{100}$ olefins, derived from GC analysis, including the amount of solids.

As can be seen from the experimental data in Table 1 ligands having the formula $(R^1)_2P$—$P(R^1)_m(R^2)_n$=$N(R^3)$ or $P(R^1)_m(R^2)_n$—$P(R^1)_2$=$N(R^3)$ wherein m=0, n=2, $R^1$=o-anisyl, $R^2$=phenyl or cyclohexyl, $R^3$=Me (Examples 1 to 4) show an attractive combination of high activity and high combined 1-hexene and 1-octene selectivity and low solids formation, even at high temperatures (>70° C.). This is contrast to ligands having a different pattern of $R^1$/$R^2$ or $R^3$ groups as per Comparative Example 5. It is noteworthy that comparative ligand G, which differs from comparative ligand B in its predominant P—P=N structure and in $R^3$ (for ligand G, $R^3$ is isopropyl rather than methyl), gives a two orders of magnitude lower activity than ligand B (Comparative Example 8), an increased amount of solids, but a similar 1-hexene and 1-octene selectivity under similar reaction conditions. It is also worth noting that ligand E, which differs from comparative ligand D in its predominant P—P=N structure and in $R^3$ (for ligand E, $R^3$ is methyl rather than isopropyl) gives a twice as high activity and a higher 1-octene selectivity than ligand D. It should be mentioned that comparative ligand C, having a predominant P—N—P structure, an isopropyl group on N and two phenyl groups on each P, also shows a higher 1-octene selectivity than comparative ligand D, but at the expense of increased solids formation at elevated temperatures (>70° C.). Thus, the catalyst activity towards selective production of 1-hexene and 1-octene at high temperatures (>70° C.) is greatly enhanced when two ortho-anisyl groups are present on one of the phosphorus atoms (see Examples 6 and 7 of Table 1 for Comparison).

The invention claimed is:

1. A ligand having the general formula (I):

(I)

wherein $R^3$ is selected from hydrogen, a hydrocarbyl group, a substituted hydrocarbyl group, a heterohydrocarbyl group, a substituted heterohydrocarbyl group, or a silyl group;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2.

2. The ligand of claim 1 wherein $R^3$ is selected from $C_1$-$C_{15}$ alkyl groups, substituted $C_1$-$C_{15}$ alkyl groups, $C_2$-$C_{15}$ alkenyl groups, substituted $C_2$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups.

3. The ligand of claim 1 wherein m is 0 and n is 2.

4. The ligand of claim 1 wherein the $R^2$ groups are independently selected from substituted or unsubstituted aromatic groups, including substituted or unsubstituted heteroaromatic groups, which do not contain a polar substituent at any of the ortho-positions.

5. The ligand of claim 1 wherein the $R^1$ group is independently selected from substituted or unsubstituted aromatic groups bearing an optionally branched $C_1$-$C_{20}$ alkoxy group on at least one of the ortho-positions.

6. A ligand having the general formula (II):

(II)

wherein $R^3$ is selected from hydrogen, a hydrocarbyl group, a substituted hydrocarbyl group, a heterohydrocarbyl group, a substituted heterohydrocarbyl group, or a silyl group;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2.

7. The ligand of claim 6 wherein $R^3$ is selected from $C_1$-$C_{15}$ alkyl groups, substituted $C_1$-$C_{15}$ alkyl groups, $C_2$-$C_{15}$ alkenyl groups, substituted $C_2$-$C_{15}$ alkenyl groups, $C_3$-$C_{15}$ cycloalkyl groups, substituted $C_3$-$C_{15}$ cycloalkyl groups, $C_5$-$C_{15}$ aromatic groups, substituted $C_5$-$C_{15}$ aromatic groups, $C_1$-$C_{15}$ alkoxy groups and substituted $C_1$-$C_{15}$ alkoxy groups.

8. The ligand of claim 6 wherein m is 0 and n is 2.

9. The ligand of claim 6 wherein the $R^2$ groups are independently selected from substituted or unsubstituted aromatic groups, including substituted or unsubstituted heteroaromatic groups, which do not contain a polar substituent at any of the ortho-positions.

10. The ligand of claim 6 wherein the $R^1$ group is independently selected from substituted or unsubstituted aromatic groups bearing an optionally branched $C_1$-$C_{20}$ alkoxy group on at least one of the ortho-positions.

11. A process of preparing a ligand having the general formula (I):

(I)

or having the general formula (II):

(II)

wherein $R^3$ is selected from hydrogen, a hydrocarbyl group, a substituted hydrocarbyl group, a heterohydrocarbyl group, a substituted heterohydrocarbyl group, or a silyl group;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2;

which comprises reacting:

(i) a compound of formula (III):

(III)

wherein X is a halide; and (ii) a compound of formula (IV):

(IV)

in the presence of an HX-acceptor.

12. A process of preparing a ligand having the general formula (I):

(I)

or having the general formula (II):

(II)

wherein $R^3$ is selected from hydrogen, a hydrocarbyl group, a substituted hydrocarbyl group, a heterohydrocarbyl group, a substituted heterohydrocarbyl group, or a silyl group;

the $R^1$ groups are independently selected from an optionally substituted aromatic group bearing a polar substituent on at least one of the ortho-positions; and the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;

with the proviso that m is 0 or 1, n is 1 or 2 and the total of m+n is 2;

which comprises reacting:

(i) a compound of formula (III):

(III)

wherein X is a halide; and
(ii) a compound of formula (IV):

$(R^1)_2P\text{—}N(R^3)H$ (IV)

in the presence of an HX-acceptor.

13. A process of preparing a ligand having the general formula (I):

$(R^1)_2P\text{—}P(R^1)_m(R^2)_n\text{=}N(R^3)$ (I)

or having the general formula (II):

$P(R^1)_m(R^2)_n\text{—}P(R^1)_2\text{=}N(R^3)$ (II)

wherein $R^3$ is selected from hydrogen, a hydrocarbyl group, a substituted hydrocarbyl group, a heterohydrocarbyl group, a substituted heterohydrocarbyl group, or a silyl group;
the $R^1$ groups are independently selected from an optionally substituted aromatic group bearing a polar substituent on at least one of the ortho-positions; and
the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;
with the proviso that m is 0 or 1, n is 1 or 2 and the total of m+n is 2;
which comprises reacting:
(i) a compound of formula (V):

$X\text{—}P(R^1)_2$ (V)

wherein X is a halide; and
(ii) a compound of formula (VI):

$(R^1)_m(R^2)_nP\text{—}N(R^3)H$ (VI)

in the presence of an HX-acceptor.

14. A ligand system prepared by reacting:
(i) a compound of formula (III):

$X\text{—}P(R^1)_m(R^2)_m$ (III)

wherein X is a halide;
wherein $R^3$ is selected from hydrogen, a hydrocarbyl group, a substituted hydrocarbyl group, a heterohydrocarbyl group, a substituted heterohydrocarbyl group, or a silyl group;
the $R^1$ groups are independently selected from an optionally substituted aromatic group bearing a polar substituent on at least one of the ortho-positions; and
the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;
with the proviso that m is 0 or 1, n is 1 or 2 and the total of m+n is 2;
and
(ii) a compound of formula (IV):

$(R^1)_2P\text{—}N(R^3)H$ (IV)

in the presence of an HX-acceptor.

15. A ligand system prepared by reacting:
(i) a compound of formula (V):

$X\text{—}P(R^1)_2$ (V)

wherein X is a halide;
wherein $R^3$ is selected from hydrogen, a hydrocarbyl group, a substituted hydrocarbyl group, a heterohydrocarbyl group, a substituted heterohydrocarbyl group, or a silyl group;
the $R^1$ groups are independently selected from an optionally substituted aromatic group bearing a polar substituent on at least one of the ortho-positions; and
the $R^2$ groups are independently selected from hydrocarbyl, substituted hydrocarbyl, heterohydrocarbyl and substituted heterohydrocarbyl groups with the proviso that when the group is aromatic it does not contain a polar substituent at any of the ortho-positions;
with the proviso that m is 0 or 1, n is 1 or 2 and the total of m+n is 2; and
(ii) a compound of formula (VI):

$(R^1)_m(R^2)_nP\text{—}N(R^3)H,$ (VI)

in the presence of an HX-acceptor.

16. The ligand of claim 1 wherein the $R^2$ groups are independently selected from optionally substituted phenyl groups which do not contain a polar substituent at any of the ortho-positions.

17. The ligand of claim 1 wherein the $R^1$ group is an o-anisyl group.

18. The ligand of claim 6 wherein the $R^2$ groups are independently selected from optionally substituted phenyl groups which do not contain a polar substituent at any of the ortho-positions.

19. The ligand of claim 6 wherein the $R^1$ group is an o-anisyl group.

* * * * *